(12) United States Patent
Fischer et al.

(10) Patent No.: US 6,623,752 B1
(45) Date of Patent: Sep. 23, 2003

(54) PATCH FOR TRANSDERMAL APPLICATION FOR PERGOLID

(75) Inventors: Wilfried Fischer, Holzkirchen (DE); Anna Sendl-Lang, Holzkirchen (DE); Dagmar Zeh-Herwerth, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 09/550,926

(22) Filed: Apr. 17, 2000

Related U.S. Application Data

(63) Continuation of application No. 09/214,209, filed on Dec. 30, 1998, now abandoned.

(30) Foreign Application Priority Data

Jul. 2, 1996 (DE) .......................................... 196 26 621

(51) Int. Cl.[7] .......................... A61K 9/70; A61K 31/355; A61F 13/00; A61F 2/00
(52) U.S. Cl. ........................ 424/449; 424/443; 424/422; 424/425; 514/458
(58) Field of Search ................................ 424/422, 425, 424/443, 449, 458

(56) References Cited

U.S. PATENT DOCUMENTS

| | | | |
|---|---|---|---|
| 4,797,405 A | | 1/1989 | Conine et al. |
| 5,114,948 A | | 5/1992 | Conine et al. |
| 5,378,730 A | * | 1/1995 | Lee et al. |
| 5,607,691 A | * | 3/1997 | Hale et al. |
| 5,656,286 A | * | 8/1997 | Miranda et al. |
| 5,738,869 A | * | 4/1998 | Fischer et al. |

FOREIGN PATENT DOCUMENTS

| | | |
|---|---|---|
| DE | 42 40 798 A1 | 6/1993 |
| EP | 0 003 667 B1 | 7/1982 |
| EP | 0 458 640 A2 | 11/1991 |
| EP | 0 204 954 B1 | 7/1992 |
| EP | 0 314 387 B1 | 8/1992 |
| GB | 2 204 240 A | 5/1988 |
| WO | WO 89/09599 | 10/1989 |
| WO | WO 91/00746 | 1/1991 |
| WO | WO 91/16885 | 11/1991 |
| WO | WO 96/04910 | 2/1996 |
| WO | WO 96/40139 | 12/1996 |

* cited by examiner

Primary Examiner—Thurman K. Page
Assistant Examiner—Amy E Pulliam
(74) Attorney, Agent, or Firm—Brooks & Kushman P.C.

(57) ABSTRACT

The invention relates to a patch for transdermal application of pergolid and its pharmaceutically acceptable salts.

8 Claims, No Drawings

PATCH FOR TRANSDERMAL APPLICATION FOR PERGOLID

This is a continuation of Ser. No. 09/214,209, filed Dec. 30, 1998, now abandoned.

The invention relates to a patch or plaster for transdermal application of pergolide and its pharmaceutically harmless salts.

Pergolide (D-6-n-propyl-8β-methylmercaptomethylergoline) is a dopamine receptor coenzyme and is administered among other things as an anti-Parkinson agent (EP-A 0 003 667), for the treatment of addition caused by psycho-stimulants (EP-A 0 204 954), and for nicotine addiction (GB-A 2 204 240). Hereafter in the disclosure, "pergolide" will be referred to as "pergolid."

Various orally administered formulations of pergolid are known from EP-A 0 003 667 and EP-A 0 527 835. The therapeutically effective daily dose is 0.01 to 20 mg.

Generally it can be said that the biological activity of drugs administered orally or intravenously is often unsatisfactory. The hepatic metabolism of the drug upon the first passage through the liver can lead to undesired concentrations and toxic by-products, or to the loss of or reduction of effect. Compared to oral administration, the transdermal administration of drugs or agents has various advantages. The drug supply can be better controlled over a longer time interval, whereby significant blood plasma fluctuation is avoided. In addition, the required therapeutic dosage can usually be distinctly reduced. Furthermore, a patch is often more preferred by the patient than one or more tablets to be taken daily.

In oral application, pergolid has a low bio-activity. Consequently, it is difficult to achieve a constant blood plasma level over a longer time period, so that three doses daily are required.

The object of the present invention is to provide a transdermal system for the systematic application of pergolid or one of its pharmaceutically harmless salts where the drawbacks of oral administration forms are avoided.

The object underlying the invention is now solved with a transdermal therapeutic system with an amount of pergolid or one of its pharmaceutically harmless salts.

The agent pergolid can be applied as a free pergolid base, pergolid mesylate and/or pergolid hydrochloride.

Pergolid or one of its pharmaceutically acceptable salts as the active agent can also be used in combination with one or more further known substances, particularly in two-fold or three-fold combinations. These further known agents can modify, enhance, synergize or alter the potency of the pergolid effect. For example, dopamine coenzymes can be provided.

Particularly suitable further agents include levodopa, carbidopa, selegeline, tracrine, physostingmine, galanthamine, 1-hydroxytacrine and/or chemical derivatives thereof, metabolites thereof and/or pharmaceutically acceptable salts thereof.

Suitable permeation promoters include singly and/or multi-valent aliphatic, cycloaliphatic and/or aromatic-aliphatic alcohols with up to 8 C atoms, for example ethanol, 12-propandiol, dexpanthenol and/or polyethylene glycol, alcohol/water mixtures: saturated and/or unsaturated fatty alcohols with 8 to 18 carbon atoms; saturated and/or unsaturated fatty acids with 8 to 18 carbon atoms; their esters; natural vitamin E; synthetic vitamin E; and/or vitamin E derivatives.

Since pergolid is light-sensitive to a certain extent, stabilizers can be employed, for example as is known from U.S. Pat. No. 5,114,948 or EF-B 0 314 387. Examples include polyvinylpyrrolidone, alpha-tocopherolsuccinate, propylgallate, methionine, cysteine and/or cysteine hydrochloride.

The transdermal therapeutic system according to the invention can be a patch, particularly with an impermeable cover layer and removable protection layer, especially a matrix system or a membrane system.

The cover layer can be polyester, polypropylene, polyethylene or polyurethane, optionally provided with a metallisation or pigment. The removeable protection layer can be polyesters polypropylene or paper with a silicone and/or polyethylene coating.

The transdermal therapeutic system according to the invention may be a matrix patch with

- an impermeable cover layer
- a drug-containing self-adhesive matrix layer or a drug-containing matrix layer which is coated with an adhesive,
- a removeable protection layer and
- pergolid or one of its pharmaceutically acceptable salts as the active agent (drug),
- optionally with further active agents and/or permeation promoters and/or stabilisers.

The matrix can be based on polyacrylate, silicone, polyisobutylene, butyl rubber, styrene/butadiene copolymer or styrene/isoprene copolymer. Such matrix materials common in the medical field are known in the prior art. Examples of acrylate adhesives include DuroTak adhesives.

A further embodiment of the invention relates to a membrane system including

- an impermeable cover layer,
- a drug-containing reservoir or a drug-containing reservoir layer,
- a semi-permeable membrane,
- a facultative adhesive layer,
- a removeable protection layer and
- pergolid or one of its pharmaceutically acceptable salts,
- optionally, further active agents and/or permeation promoters, stabilisers, emulsifying agents, thickening agents and/or common membrane system or reservoir patch additives.

The drug-containing reservoir layer can thus be provided in an intermediate space formed between the covering layer and the membrane. The reservoir is filled with the active agents (drug) and facultative additives.

Inert polymers are suitable for the membrane, particularly on the basis of polypropylene, polyvinylacetate or silicone When a membrane is provided, it can have the effect of controlling drug release depending on the pore size.

In the following, the invention is illustrated through examples.

EXAMPLE 1

Matrix Patch

The following components are dispersed in a sufficient amount of ethyl acetate:

| | |
|---|---|
| pergolid | 10 g |
| natural vitamin E | 10 g |
| propylene glycol | 15 g |

-continued

| | |
|---|---|
| acrylate adhesive (as 35% solution in ethyl acetate e.g. DuroTak 326-1753) | 65 g |

In a commercial coating machine, the obtained dispersion is applied to a silicone-treated polypropylene foil, which results in a surface weight of the dried drug-containing adhesive matrix of 100 g/m². In a coating station, a 50 μm thick polyurethane foil is applied. Thereafter, 20 cm² or Optionally 10, 30, 40 or 50 cm² patches are stamped out of the laminate.

EXAMPLE 2

Reservoir TTS

The following components are dispersed in ethanol/water;

pergolid (or a corresponding amount of pergolid salts, e.g. pergolid mesylate) 5 to 10% optionally, natural vitamin E and/or polyvinylpyrrolidone as stabiliser.

For the production of the patches, the following elements are foreseen:

covering layer or for example polyethylene semi-permeable membrane, e.g. CoTan 9711 adhesive for adhesive layer, e.g. Duro-Tak 326-1753 removeable protection layer, e.g. Gelroflex.

In a first step, a laminate is produced in a common machine with the adhesive, the membrane and the protection layer. In a second step, an empty TTS is produced from the laminate and the covering layer. In a third step, the empty TTS is filled with the active agent dispersion. In a fourth step, the filled TTS is closed and in a fifth step patches are stamped out in the desired size.

What is claimed is:

1. A pergolide transdermal therapeutic system, comprising
    a) a polymer matrix comprising a polyacrylate polymer;
    b) as the active ingredient, a pergolide active ingredient selected from the group consisting of pergolide, a therapeutically acceptable salt thereof, and mixtures thereof;
    c) a permeation promoter selected from the group consisting of natural vitamin E, synthetic vitamin E, vitamin E derivatives, and mixtures thereof.

2. The pergolide transdermal therapeutic system of claim 1, wherein said pergolide active ingredient is selected from the group consisting of pergolide free base, pergolide mesylate, or pergolide hydrochloride.

3. The pergolide transdermal therapeutic system of claim 1, further comprising a stabilizer selected from the group consisting of α-tocopherol succinate, propylgallate, methionine, cysteine, and cysteine hydrochloride.

4. The pergolide transdermal therapeutic system of claim 1 in the form of a patch with an impermeable cover layer and removable protection layer.

5. A pergolide transdermal therapeutic system, comprising
    a) a polymer matrix comprising a polyacrylate;
    b) as therapeutically active ingredients, an active ingredient composition consisting of a dopamine coenzyme and at least one of pergolide or a therapeutically acceptable salt thereof, wherein said dopamine coenzyme and said pergolide or therapeutically acceptable salt thereof are different;
    c) a permeation promoter selected from the group consisting of natural vitamin E, synthetic vitamin E, vitamin E derivatives, and mixtures thereof.

6. The pergolide transdermal therapeutic system of claim 5, wherein said pergolide active ingredient is selected from the group consisting of pergolide free base, pergolide mesylate, or pergolide hydrochloride.

7. The pergolide transdermal therapeutic system of claim 5, further comprising a stabilizer selected from the group consisting of α-tocopherol succinate, propylgallate, methionine, cysteine, and cysteine hydrochloride.

8. A pergolide transdermal therapeutic system, comprising
    a) a polymer matrix comprising a polyacrylate polymer;
    b) as the active ingredient, a pergolide active ingredient selected from the group consisting of pergolide, a therapeutically acceptable salt thereof, and mixtures thereof;
    c) a first permeation promoter selected from the group consisting of natural vitamin E, synthetic vitamin E, vitamin E derivatives, and mixtures thereof;
    d) a second permeation promoter selected from the group consisting of ethanol, aliphatic monols other than ethanol, cycloaliphatic monols, and arylaliphatic monols.

* * * * *